United States Patent [19]

Heath

[11] Patent Number: 5,762,497
[45] Date of Patent: Jun. 9, 1998

[54] ENDODONTIC DENTAL INSTRUMENT

[75] Inventor: Derek E. Heath, Johnson City, Tenn.

[73] Assignee: Tulsa Dental Products, Tulsa, Okla.

[21] Appl. No.: 612,058

[22] Filed: Mar. 7, 1996

[51] Int. Cl.$^6$ ........................................... A61C 5/02
[52] U.S. Cl. ............................................... 433/102
[58] Field of Search .................... 433/102, 224, 433/165

[56] References Cited

U.S. PATENT DOCUMENTS

| | | | |
|---|---|---|---|
| 4,836,780 | 6/1989 | Buchanan | 433/102 |
| 4,934,934 | 6/1990 | Arpaio, Jr. et al. | 433/102 |
| 5,106,298 | 4/1992 | Heath et al. | 433/102 |
| 5,387,059 | 2/1995 | Borzemsky | 433/165 |
| 5,464,362 | 11/1995 | Heath et al. | 433/102 |

*Primary Examiner*—Cary E. O'Connor
*Attorney, Agent, or Firm*—Bell Seltzer Intellectual Property Law Group of Alston & Bird llp

[57] ABSTRACT

An endodontic instrument which comprises an elongate shank which has a tapered working length adjacent the pilot end, and at least one continuous helical flute formed along the tapered working length so as to define sharp cutting edges along the sides of the flutes. Also, at least one relief, in the form of a flat surface, extends axially along a substantial portion of the length of the working length, which acts to reduce the tendency of the tapered working length to screw into and crack the tooth during manipulation thereof by the dentist in the course of root canal therapy.

15 Claims, 2 Drawing Sheets

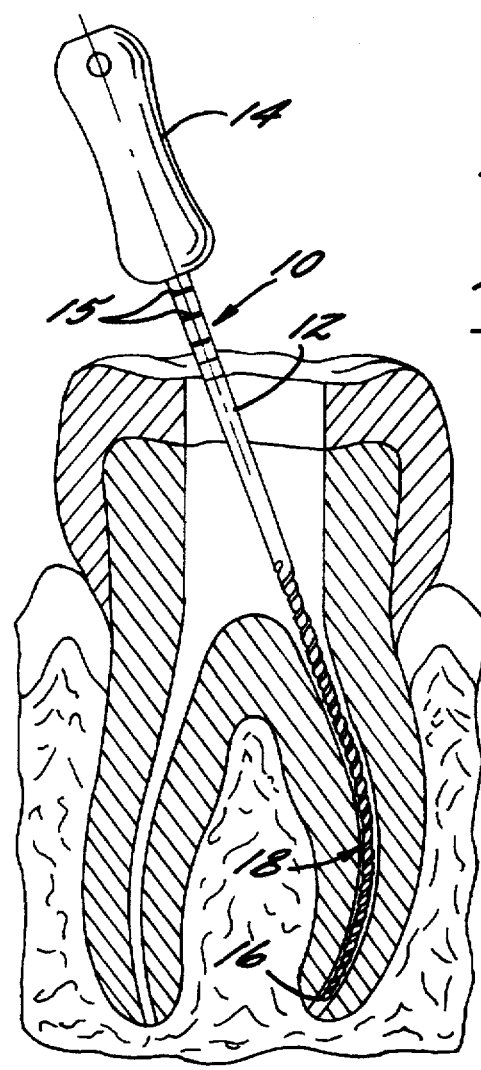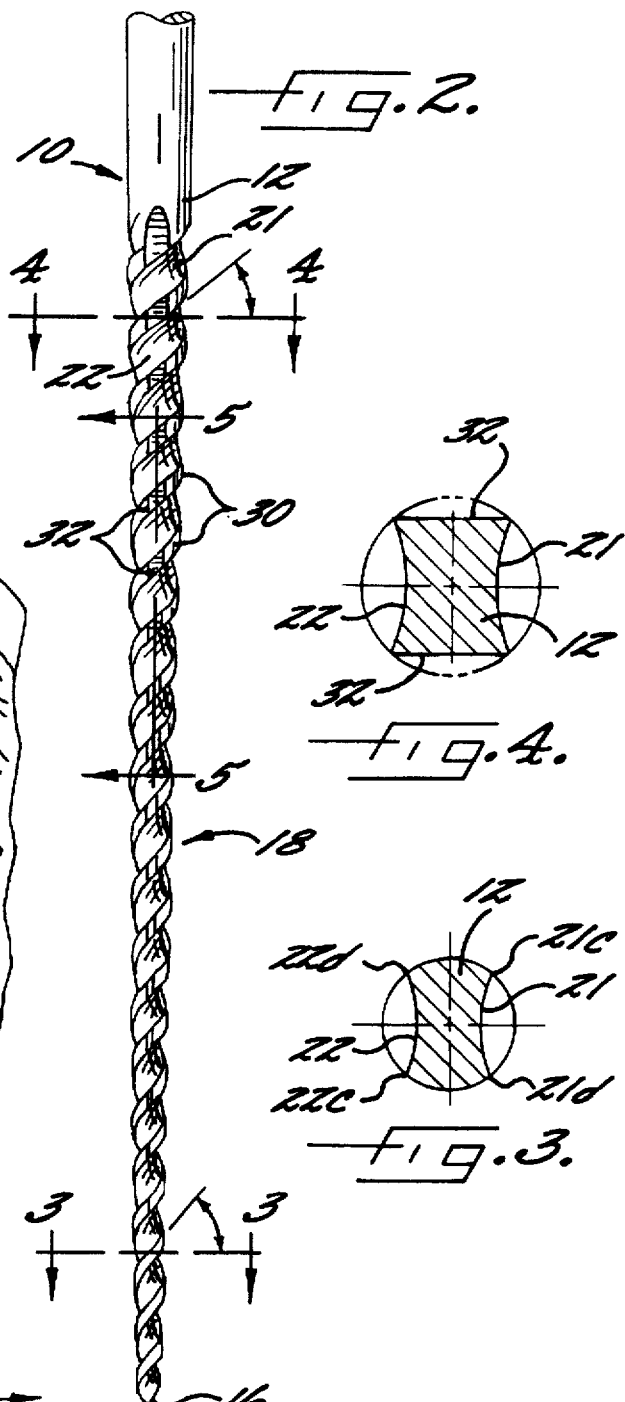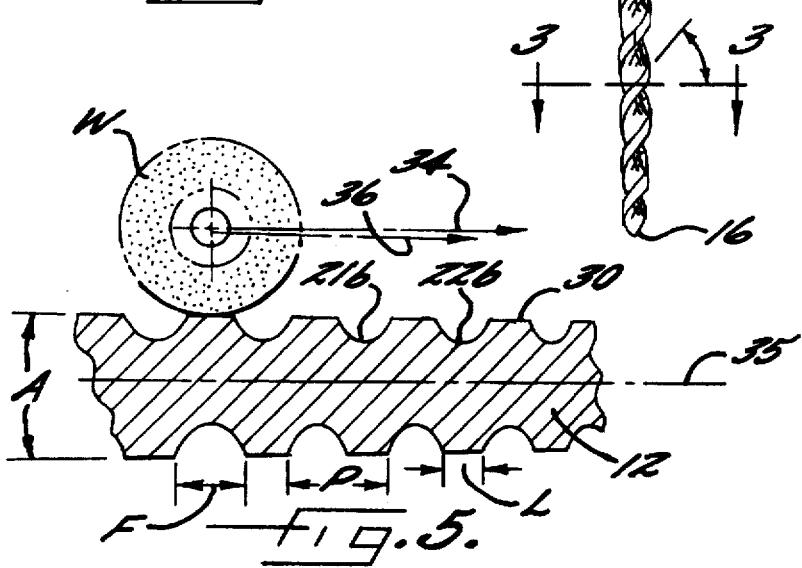

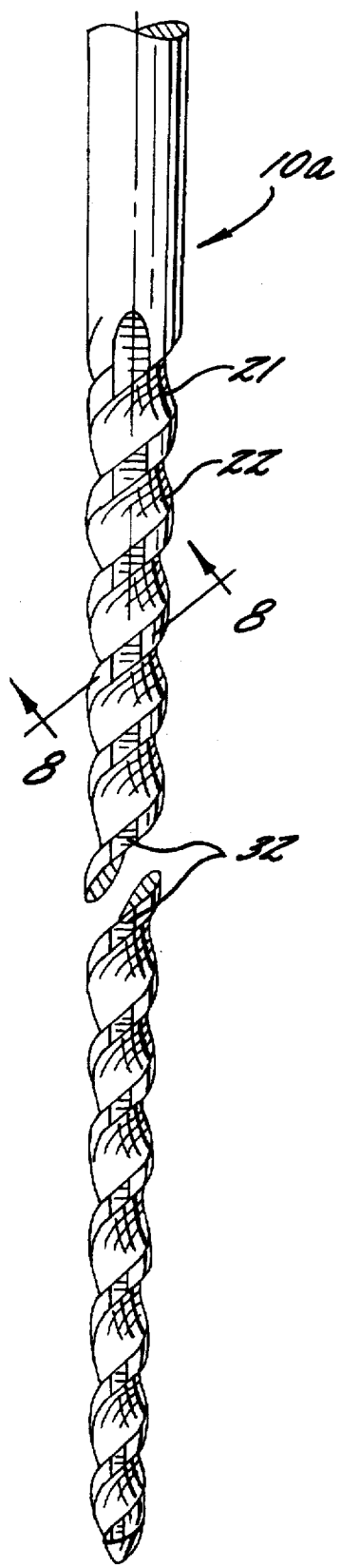
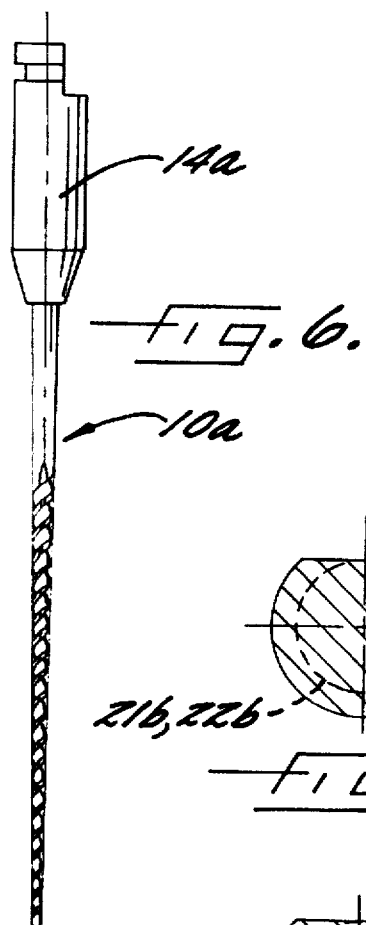
Fig. 6.
Fig. 7.
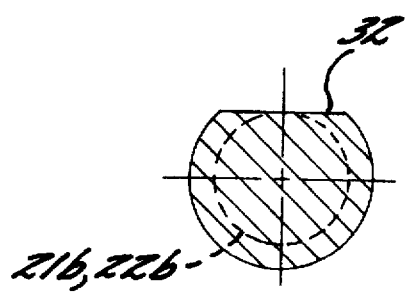
Fig. 8.
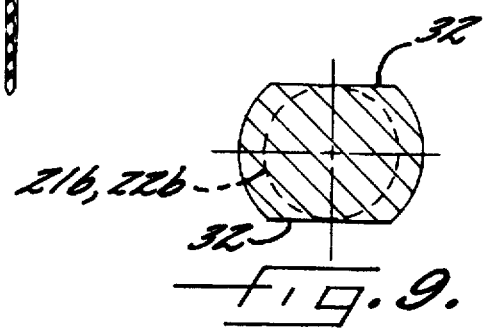
Fig. 9.
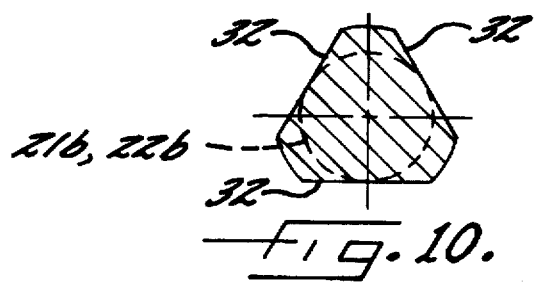
Fig. 10.

ENDODONTIC DENTAL INSTRUMENT

BACKGROUND OF THE INVENTION

The present invention relates to an endodontic instrument adapted for use in performing root canal therapy on teeth.

Root canal therapy is a well-known procedure wherein the crown of the diseased tooth is opened so as to permit the canal to be cleaned and then filled. More particularly, a series of very delicate, flexible, finger held instruments or files are used to clean out and shape the root canal, and each file is rotated and reciprocated in the canal by the dentist, either manually or with the use of a dental handpiece which mounts the file. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown may be fitted to the tooth.

Endodontic files of the described type are fully disclosed in U.S. Pat. Nos. 4,934,934 and 5,464,362, the disclosures of which are incorporated herein by reference. Such files comprise an elongate rod-like shank having a handle at one end, and with one or more, up to four, helical flutes formed in the peripheral surface of the shank. The files are commonly supplied to the clinician in kits which comprise several files of increasing diameter. In particular, and in accordance with ANSI/ADA Specification No. 28-1988, files are provided in diameters which range from 0.08 mm at the tip (size 08) to 1.40 mm at the tip (size 140), and the files are provided in kits which contain a number of files of increasing diameter so that the files from a particular kit may be used in sequence by the clinician in accordance with the requirements of the particular canal being cleaned.

Also, in conventional kits, the working length of each file in the kit is tapered, with the angle of the taper being conventionally indicated as mm diameter increase per mm in length (hereinafter mm/mm). Specifically, kits of instruments with the following tapers are commonly available:

1) 0.02 mm/mm (i.e. about 1° included angle)

2) 0.04 mm/mm (i.e. about 2° included angle)

3) 0.06 mm/mm (i.e. about 3° included angle)

4) 0.08 mm/mm (i.e. about 4° included angle)

It has been found that as the cutting instruments become more steep (e.g., size 0.06 and above), the helix angle of the flutes at the top of the taper becomes steeper, causing the instrument to screw into the canal during its manipulation in the canal. This is dangerous, since the instrument then tends to screw into the canal, causing a wedging action which can split the tooth.

It is accordingly an object of the present invention to provide an endodontic instrument of the described type which has a reduced tendency to screw into the canal and split the tooth, even in the case of instruments having a relatively steep taper.

SUMMARY OF THE INVENTION

The above and other objects and advantages of the present invention are achieved in the embodiments illustrated herein by the discovery that the tendency of highly tapered endodontic instruments to screw into and split the tooth can be alleviated by forming one or more axial reliefs or flats in the cutting surface. More particularly, the present invention involves an endodontic instrument which comprises an elongate shank having a proximate end and an opposite pilot end, and a working length adjacent the pilot end. At least one continuous helical flute is formed so as to extend along the length of the working length, and at least one relief extends axially along at least a substantial portion of the length of the working length.

In one preferred embodiment, the flute defines a curved concave wall when viewed in transverse cross section and a sharp cutting edge along each side edge of the curved concave wall. Also, a helical land is positioned between axially adjacent flute segments, with the land having a width which is equal to at least about 15% of the pitch of the flute when viewed in longitudinal cross section. Further, the relief defines a chord line when viewed in transverse cross section and extends to a depth which is equal to at least about one-half the depth of the flute.

The presence of the relief in the working length of the instrument as described above has been found to reduce the tendency of the instrument to screw into the canal of the tooth, particularly in the larger diameter portion of the shank which is adjacent the proximate end of the shank, and thus the danger of splitting the tooth is minimized. The relief also reduces the mass of the instrument, and provides additional flexibility.

BRIEF DESCRIPTION OF THE DRAWINGS

Some of the objects and advantages of the present invention having been stated, others will appear as the description proceeds, when taken in conjunction with the accompanying drawings, in which FIG. 1 is a sectional view of a tooth having two roots, with an endodontic instrument which embodies the present invention received in one of the roots.

FIG. 2 is an enlarged perspective view of the lower portion of the instrument shown in FIG. 1;

FIG. 3 is a transverse sectional view taken substantially along the line 3—3 of FIG. 2;

FIG. 4 is a longitudinal sectional view taken substantially along the line 4—4 of FIG. 2;

FIG. 5 is a longitudinal cross-sectional view of a portion of the instrument, and schematically indicating the process of forming a relief on the peripheral surface in accordance with the present invention;

FIG. 6 shows a second embodiment of an endodontic instrument in accordance with the present invention, and which is adapted for attachment to a dental handpiece;

FIG. 7 is an enlarged perspective view of the lower portion of the instrument shown in FIG. 6;

FIG. 8 is a transverse sectional view taken substantially along the line 8—8 of FIG. 7; and FIGS. 9 and 10 are views similar to FIG. 8 but illustrating additional embodiments of the invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Referring more particularly to FIGS. 1-4, an endodontic instrument 10 is illustrated which comprises a shank 12 which is preferably composed of a metallic material such as stainless steel, or nickel-titanium alloy as described in U.S. Pat. No. 5,464,362. In one preferred embodiment, the shank is composed of an alloy comprising at least about 40% titanium and at least about 50% nickel. Also, the shank 12 is of circular cross-sectional configuration, and it typically has a length of about 30 mm (1.2 inches). The shank also includes an outer or proximate end which mounts a conventional handle 14, which is configured for hand engagement, and the portion of the shank immediately below the handle includes calibrated depth markings 15 of conventional design. The shank further includes an opposite distal or pilot end 16, and a tapered working length 18 is defined adjacent the pilot end 16. The working length 18 may have a length of from about 2 mm (0.08 inches) up to the full length of the shank 12, i.e. about 30 mm (1.2 inches). However, in the illustrated embodiment, the working length 18 has a length sufficient to extend substantially the full depth of a tooth root canal as illustrated in FIG. 1, which is about 16 mm (0.63 inches).

The outer peripheral surface of the working length 18 is tapered, so as to define an included angle A (FIG. 5) of between about ½ and 4 degrees. Also, in the illustrated embodiment, the working length 18 includes two continuous helical flutes 21, 22 formed in the peripheral surface, and as best seen in FIGS. 3 and 4, each of the flutes 21, 22 defines a curved concave wall when viewed in transverse cross section, and each wall includes a pair of helical shoulders 21c, 21d, and 22c, 22d, at the peripheral surface and which face in generally opposite axial directions. The shoulders 21c, 21d, 22c, 22d each intersect the periphery of the shank at an angle of about 90° to a tangent to the shank at the point of intersection, to form what is commonly referred to as a substantially zero or neutral rake angle. Stated in other words, each shoulder lies substantially on a radius of the shank as seen in FIG. 3, so as to form a sharp cutting edge. Each of the flutes also defines a bottom or base 21b, 22b, (FIG. 5) respectively, at the point of maximum depth from the peripheral surface.

The peripheral surface of the working length 18 further comprises a helical land 30 which is positioned between axially adjacent flute segments. The flutes are preferably of uniform pitch P (FIG. 5), which is defined herein as the distance between corresponding points of adjacent flute segments. In a typical example, the length of the working length 18 is about 0.63 inches, with a total of about 18 flute spirals extending along the entire length of the pilot end portion, such that the pitch P is 0.63/18 or about 0.035 inches. In the illustrated embodiment, the depth of the flutes increased from the pilot end 16 toward the proximate end at the handle 14. As a result, the width F of the flutes, and the width L of the lands 30, will inversely vary somewhat along the length of the pilot end portion. For example, in the above example, the width F of the flutes is about 0.03 inches and the width L of lands 30 is about 0.005 inches at the upper end of the working length adjacent the handle 14, and the width W is about 0.025 inches and the width L is about 0.01 inches adjacent the pilot end 16. As will be apparent, the width L of the lands 30 is equal to a significant portion of the pitch P, which is preferably equal to at least about 15% of the pitch P. In the above example, the width L varies from about 14.2% of the pitch P adjacent the upper end to about 28.5% of the pitch P adjacent the pilot end 16. This is desirable in that the relatively broad lands 30 prevent undue cutting by the instrument laterally into the wall of the canal during manipulation of the instrument by the dentist.

The instrument as illustrated in FIGS. 1-4 also includes two oppositely facing reliefs 32 which are formed in the peripheral surface along a substantial portion of the length of the working length 18. As best seen in FIG. 4, each relief 32 defines a chord line which has a maximum depth which is equal to about one-half the depth of the base 21b, 22b of each of the flutes.

FIG. 5 schematically illustrates a process for forming the reliefs 32, and wherein a grinding wheel W (shown in a greatly reduced scale) is advanced axially along the peripheral surface. As illustrated, the wheel W advances along a line 34 which is parallel to the central axis 35 of the elongate shank of the instrument, and such that the relief 32 defines a plane which is substantially parallel to the central axis 35. This also results in the relief 32 having a relatively significant depth in the portion of the working length 18 adjacent the proximate end, and with the depth diminishing toward the pilot end 16.

The line 36 in FIG. 5 schematically illustrates that the grinding wheel may be moved along a line which is parallel to a line corresponding to the taper of the working length 18. This results in the reliefs 32 each being of substantially uniform depth along the length of the working length, and as illustrated in the embodiments of FIGS. 6-10. Movement along a line which is intermediate or somewhat outside the lines and is also possible.

The embodiment of FIGS. 6-10 is adapted for machine use, and the instrument 10a includes a head or handle 14a which is configured for attachment to a conventional dental handpiece. Also, FIGS. 8-10 illustrate that the peripheral surface of the instrument may include one, two, or three of the reliefs 32 as described above. In these embodiments, the reliefs are shown as having a maximum depth which is substantially equal to the depth of the base 21a, 22b of the two flutes.

In the drawings and the specification, there has been set forth preferred embodiments of the invention and, although specific terms are employed, the terms are used in a generic and descriptive sense only and not for the purpose of limitation, the scope of the invention being set forth in the following claims.

That which is claimed is:

1. An endodontic instrument adapted for use in performing root canal therapy on a tooth, and comprising an elongate shank having a proximate end and an opposite pilot end, and so as to define a working length adjacent said pilot end which includes a peripheral surface, at least one continuous helical flute formed so as to extend along the length of said working length, and at least one relief extending axially along at least a substantial portion of the length of said working length, wherein when viewed in transverse cross section, said peripheral surface defines a circle and said one relief defines a chord line which intersects the circle, and wherein said at least one flute defines a base at the point of maximum depth from the peripheral surface, and said chord line has a maximum depth which is at least equal to about one half the depth of said base of said one flute along at least a substantial portion of the length of said one flute.

2. The endodontic instrument as defined in claim 1 wherein said peripheral surface is tapered toward said pilot end at an included angle of between about ½ and about 4 degrees.

3. The endodontic instrument as defined in claim 2 wherein said elongate shank defines a central axis, and said relief defines a plane which is substantially parallel to said central axis.

4. The endodontic instrument as defined in claim 2 wherein said elongate shank defines a central axis, and said relief defines a plane which is substantially parallel to a line corresponding to the taper of said peripheral surface.

5. The endodontic instrument as defined in claim 1 wherein said peripheral surface of said working length comprises a helical land which is positioned between axially adjacent flute segments, and wherein said helical land has a width which is equal to at least about 15% of the pitch of said one flute when viewed in longitudinal cross section.

6. The endodontic instrument as defined in claim 5 wherein said helical land lies along an arc of a circle when viewed in transverse cross section.

7. The endodontic instrument as defined in claim 1 wherein said one helical flute defines a curved concave wall when viewed in transverse cross section.

8. The endodontic instrument as defined in claim 7 wherein said one flute defines a pair of helical shoulders at the peripheral surface of said pilot end portion and which face in generally opposite axial directions, and wherein each of said helical shoulders has a substantially neutral rake angle.

9. The endodontic instrument as defined in claim 1 further comprising a handle mounted at said proximate end of said shank.

10. An endodontic instrument adapted for use in performing root canal therapy on a tooth, and comprising an elongate shank having a proximate end and an opposite pilot end, and so as to define a working length adjacent said pilot end which includes a peripheral surface, at least one continuous helical flute formed so as to extend along the length of said working length, with said one flute defining a curved concave wall when viewed in transverse cross section and a cutting edge along each side edge of said curved concave wall, and a helical land positioned between axially adjacent flute segments, with said helical land having a width which is equal to at least about 15% of the pitch of said one flute when viewed in longitudinal cross section, and at least one relief extending axially along at least the portion of the length of said working length of said peripheral surface which is adjacent said proximate end, with said relief extending to a depth which is equal to at least about one-half the depth of said one flute.

11. The endodontic instrument as defined in claim 10 wherein said peripheral surface is tapered toward said pilot end at an included angle of between about ½ and about 4 degrees.

12. The endodontic instrument as defined in claim 11 wherein, when viewed in transverse cross section, said peripheral surface defines a circle and said one relief defines a chord line which intersects said circle.

13. The endodontic instrument as defined in claim 12 wherein at least two of said continuous helical flutes are formed in said peripheral surface, and at least two of said reliefs are formed in said peripheral surface.

14. The endodontic instrument as defined in claim 10 wherein said shank is composed of an alloy which comprises at least about 40% titanium and at least about 50% nickel.

15. An endodontic instrument adapted for use in performing root canal therapy on a tooth, and comprising an elongate shank having a proximate end and an opposite pilot end, and so as to define a working length adjacent said pilot end which includes a peripheral surface, at least one continuous helical flute formed so as to extend along the length of said working length, at least one relief extending axially along at least a substantial portion of the length of said working length, wherein said peripheral surface is tapered toward said pilot end at an included angle of between about ½ and about 4 degrees, and wherein said elongate shank defines a central axis, and said relief defines a plane which is substantially parallel to said central axis.

* * * * *